US011013919B2

(12) United States Patent
Eskandar et al.

(10) Patent No.: US 11,013,919 B2
(45) Date of Patent: May 25, 2021

(54) SYSTEMS AND METHODS FOR CONTROLLING BRAIN ACTIVITY

(71) Applicant: The General Hospital Corporation, Boston, MA (US)

(72) Inventors: Emad N. Eskandar, Nahant, MA (US); Alik S. Widge, Somerville, MA (US); Darin D. Dougherty, Wellesley, MA (US); Meng-Chen Lo, Boston, MA (US); Ishita Basu, Boston, MA (US)

(73) Assignee: The General Hospital Corporation, Boston, MA (US)

( * ) Notice: Subject to any disclaimer, the term of this patent is extended or adjusted under 35 U.S.C. 154(b) by 1 day.

(21) Appl. No.: 16/312,446

(22) PCT Filed: Jun. 23, 2017

(86) PCT No.: PCT/US2017/038974
§ 371 (c)(1),
(2) Date: Dec. 21, 2018

(87) PCT Pub. No.: WO2017/223430
PCT Pub. Date: Dec. 28, 2017

(65) Prior Publication Data
US 2019/0247661 A1  Aug. 15, 2019

Related U.S. Application Data

(60) Provisional application No. 62/353,927, filed on Jun. 23, 2016.

(51) Int. Cl.
*A61N 1/00* (2006.01)
*A61N 1/36* (2006.01)
(Continued)

(52) U.S. Cl.
CPC .......... *A61N 1/36082* (2013.01); *A61B 5/316* (2021.01); *A61N 1/0534* (2013.01);
(Continued)

(58) Field of Classification Search
CPC ............ A61N 1/36082; A61N 1/36146; A61N 1/36139; A61N 1/36135; A61N 1/0534;
(Continued)

(56) References Cited

U.S. PATENT DOCUMENTS 7,917,221 B2  3/2011  Tass
8,000,796 B2  8/2011  Tass et al.
(Continued)

OTHER PUBLICATIONS

Benchenane et al., Oscillations in the Prefrontal Cortex: A Gateway to Memory and Attention, Current Opinion in Neurobiology, 2011, 21(3):475-485.
(Continued)

*Primary Examiner* — Mallika D Fairchild
(74) *Attorney, Agent, or Firm* — Quarles & Brady LLP

(57) ABSTRACT

Systems and methods for controlling brain activity are provided. In some aspects, a method for controlling a synchrony in brain activity of a subject is provided. The method includes positioning stimulators to stimulate a first region and a second region of a subject's brain, and selecting a pulsed stimulation sequence comprising a first stimulation to the first region and a second stimulation to the second region, wherein the stimulations are timed to be substantially concurrent and separated by a phase lag. The method also includes delivering the pulsed stimulation sequence, using the stimulators, to control a synchrony between the first region and the second region at a predetermined frequency.

18 Claims, 11 Drawing Sheets

(51) Int. Cl.
*A61N 1/05* (2006.01)
*A61B 5/316* (2021.01)

(52) U.S. Cl.
CPC ..... *A61N 1/36135* (2013.01); *A61N 1/36139* (2013.01); *A61N 1/36146* (2013.01); *A61N 1/36153* (2013.01); *A61N 1/36171* (2013.01); *A61N 1/36178* (2013.01)

(58) Field of Classification Search
CPC ............ A61N 1/36153; A61N 1/36171; A61N 1/36178; A61B 5/04012
See application file for complete search history.

(56) References Cited

U.S. PATENT DOCUMENTS

| | | | | |
|---|---|---|---|---|
| 2001/0051819 | A1* | 12/2001 | Fischell | A61N 1/3605 607/45 |
| 2006/0276702 | A1 | 12/2006 | McGinnis | |
| 2012/0271374 | A1* | 10/2012 | Nelson | A61N 1/0534 607/45 |
| 2014/0148872 | A1* | 5/2014 | Goldwasser | A61N 1/36025 607/45 |
| 2015/0066104 | A1 | 3/2015 | Wingeier et al. | |
| 2015/0174418 | A1 | 6/2015 | Tyler et al. | |

OTHER PUBLICATIONS

Buschman et al., Serial, Covert Shifts of Attention During Visual Search are Reflected by the Frontal Eye Fields and Correlated with Population Oscillations, Neuron, 2009, 63(3):386-396.

Malone Jr. et al., Deep Brain Stimulation of the Ventral Capsule/ Ventral Striatum for Treatment-Resistant Depression, Biological Psychiatry, 2009, 65(4):267-275.

Milad et al., Fear Extinction as a Model for Translational Neuroscience: Ten Years of Progress, Annual Review of Psychology, 2012, 63:129-151.

PCT International Search Report and Written Opinion, PCT/US2017/ 038974, dated Sep. 15, 2017, 16 pages.

* cited by examiner

SYSTEMS AND METHODS FOR CONTROLLING BRAIN ACTIVITY

CROSS-REFERENCE TO RELATED APPLICATIONS

This application represents the national stage entry of PCT International Application No. PCT/US2017/038974 filed Jun. 23, 2017, which is based on, claims priority to, and incorporates herein by reference in their entirety U.S. Ser. No. 62/353,927 filed Jun. 23, 2016, and entitled "A METHOD TO ALTER OSCILLATORY SYNCHRONY BETWEEN TWO BRAIN REGIONS THROUGH OPEN-LOOP DOUBLE-SITE PAIRED ELECTRICAL STIMULATIONS."

GOVERNMENT RIGHTS

This invention was made with government support under W911NF-14-2-0045 awarded by the Defense Advanced Research Projects Agency and under R21 MH109722-01A1 awarded by the National Institutes of Health. The government has certain rights in the invention.

BACKGROUND

The present disclosure relates generally to systems and methods for controlling brain activity.

Patients suffering from mental and emotional conditions, such as post-traumatic stress disorder (PTSD), intellectual disability, autism, brain injury, depression, addiction, and others, can have severe impairments that lead to significant disability and lost productivity. Such brain disorders are thought to be caused by malfunctioning neural circuits. Often, psychiatric treatments fail to cure a substantial fraction of patients, who are then declared resistant to approved therapeutic interventions. At the core of the problem is the focus on historical diagnostic categories. The National Institute of Mental Health's (NIMH) Research Domain Criteria (RDoC) project aims to develop neuroscience-based classification schemes for diagnosis and treatment of neural circuitry dysfunction. Diagnostic and Statistical Manual (DSM) diagnoses are not neurobiologic entities, but are a historical checklist-based approach of clustering symptoms used to define hypothetical constructs or syndromes. Those syndromes may not align with underlying neurobiological dysfunction in neural circuitry and corresponding behavioral (functional) domains.

Thus, attempts have been made to treat mental and emotional disorders previously treated by psychiatrists using responsive brain stimulation systems. These approaches include stimulating a patient's brain based on brain activity or clinical features, using implantable, cortical and subcortical electrodes. In particular, there are a number of sites in the brain where stimulation has been applied in attempts to change a patient's emotional experiences. However, these responsive brain stimulation systems often have no proven biomarker. A biomarker may be a measurable indicator or signal from the brain or body representative of the symptoms of the illness being treated that indicates whether the symptoms have gotten better or worse. Without something reliable to sense, it is difficult for the responsive stimulator to respond accurately.

Further, neurologic and sensory-motor disorders also often involve dysfunctional connectivity within circuits. Parkinsons disease and other movement disorders involve abnormal oscillatory connectivity between cortex and basal ganglia. Spinal cord injury involves disconnection between motor cortex and descending control circuits.

Deep brain stimulation (DBS) is used to treat many of conditions. For instance, DBS has been used to control symptoms, such as rigidity, slowed movement, tremors, and walking difficulties, in patients with Parkinson's. Other applications include epilepsy, chronic pain, obsessive compulsive disorder, depression, and others. The procedure involves implantation of an electrical stimulator into a defined area of a patient's brain, followed by delivery of high-frequency electrical impulses (e.g. up to 24 hours per day). In some applications, DBS may be unilateral or bilateral in the subthalamic nucleus (STN), internal capsule, deep cortex, or in the globus pallidus internus (GPi) depending on the observed symptoms and treatment plan.

Although the exact mechanism of action is not well understood, it is believed that electrical currents produced by DBS interfere with or block brain activity close to the activation site. As such, DBS affords a number of advantages over traditional ablative surgery including being less invasive, reversible, and allowing for bilateral stimulation. However, recent clinical trials using DBS for a variety of indications, most particularly depression, have failed. This is in part because current DBS technologies operate at single sites, rather than affecting circuit-level functions. By contrast, synchronized neural activity, detectable as coherent oscillation in the local field potential (LFP) from different brain regions, has been recognized as an important mechanism for communication between brain networks. Such oscillations are correlated to attention, learning and memory formation, help to coordinate brain networks involves in sensory-motor function, and are often impaired in psychiatric disorders including depression, post-traumatic stress disorder (PTSD), and obsessive compulsive disorder.

Therefore, given the above, there is a need for improved systems and methods for treating patients suffering from neurological conditions that involve circuit dysfunction or dys-connectivity.

SUMMARY

The present disclosure overcomes the drawbacks of previous technologies by providing systems and methods for controlling brain activity using stimulation. In particular, a novel approach is introduced whereby a connectivity between different brain regions may be affected using paired stimulations. As will be described, in some aspects, a synchrony between brain regions may be modified using stimulations that are timed to be substantially concurrent and separated by a phase lag.

In accordance with one aspect of the disclosure, a method for controlling synchrony in brain activity of a subject is provided. The method includes positioning stimulators to stimulate a first region and a second region of a subject's brain, and selecting a pulsed stimulation sequence comprising a first stimulation to the first region and a second stimulation to the second region, wherein the stimulations are timed to be substantially concurrent and separated by a phase lag. The method also includes delivering the pulsed stimulation sequence, using the stimulators, to control a synchrony between the first region and the second region at a predetermined frequency.

In accordance with another aspect of the disclosure, a method for controlling a stimulation system is provided. The method includes receiving signals corresponding to brain activity in a first region and a second region of a subject's brain, and analyzing the signals to determine a synchrony between the first region and the second region. The method also includes generating a pulsed stimulation sequence configured to control the synchrony, wherein the stimulation sequence comprises a first stimulation to the first region and a second stimulation to the second region, with the stimulations being timed to be substantially concurrent and separated by a phase lag. The method further includes controlling a stimulation system using the pulsed stimulation sequence.

In accordance with yet another aspect of the disclosure, a system for controlling a stimulation provided to a subject. The system includes an input configured to receive signals acquired from a subject's brain, and a processor configured to receive signals from the input corresponding to brain activity in a first region and a second region of a subject's brain, and analyze the signals to determine a synchrony between the first region and the second region. The processor is also configured to determine a pulsed stimulation sequence configured to control the synchrony, wherein the stimulation sequence comprises a first stimulation to the first region and a second stimulation to the second region, with the stimulations being timed to be substantially concurrent and separated by a phase lag, and direct a signal generation module in communication with the processor to deliver the pulsed stimulation sequence.

The foregoing and other advantages of the present disclosure will appear from the following description.

BRIEF DESCRIPTION OF THE DRAWINGS

The present invention will hereafter be described with reference to the accompanying drawings, wherein like reference numerals denote like elements. The patent or application file contains at least one drawing executed in color. Copies of this patent or patent application publication with color drawing(s) will be provided by the Office upon request and payment of the necessary fee.

DETAILED DESCRIPTION

Clinical treatments of brain conditions related to faulty brain circuit connectivity are limited due to the lack of established treatment paradigms. In particular, synchronized neural activity has been recognized as an important mechanism for communication between brain networks, including for attention, learning and memory formation. These, however, are often impaired in psychiatric disorders including depression, autism, post-traumatic stress disorder (PTSD), and obsessive compulsive disorder. Related networks are impaired in movement, sensory-motor, and neuro-degenerative disorders, to which aspects of the present disclosure also apply. It is recognized herein that deep brain stimulation (DBS) can be a promising technique to help address these, and other disorders, due to due to its known safety and clinical translatability.

As such, the present disclosure provides systems and methods for controlling brain activity using stimulation, such as electrical stimulation. In particular, a novel approach is introduced whereby a synchrony between different regions of a subject's brain can be modified. Specifically, stimulation pulses delivered to different regions substantially concurrently and separated by a selectable phase lag may be used to modify synchrony at targeted frequencies. In this manner, coherence or other indicators quantifying a connectivity between two brain regions, may be increased. Furthermore, phase lag can be used to control a directionality of connectivity enhancement. This is stark contrast to previous techniques, which apply DBS at single brain sites to break down, rather than enhance brain connectivity.

Figure 1:
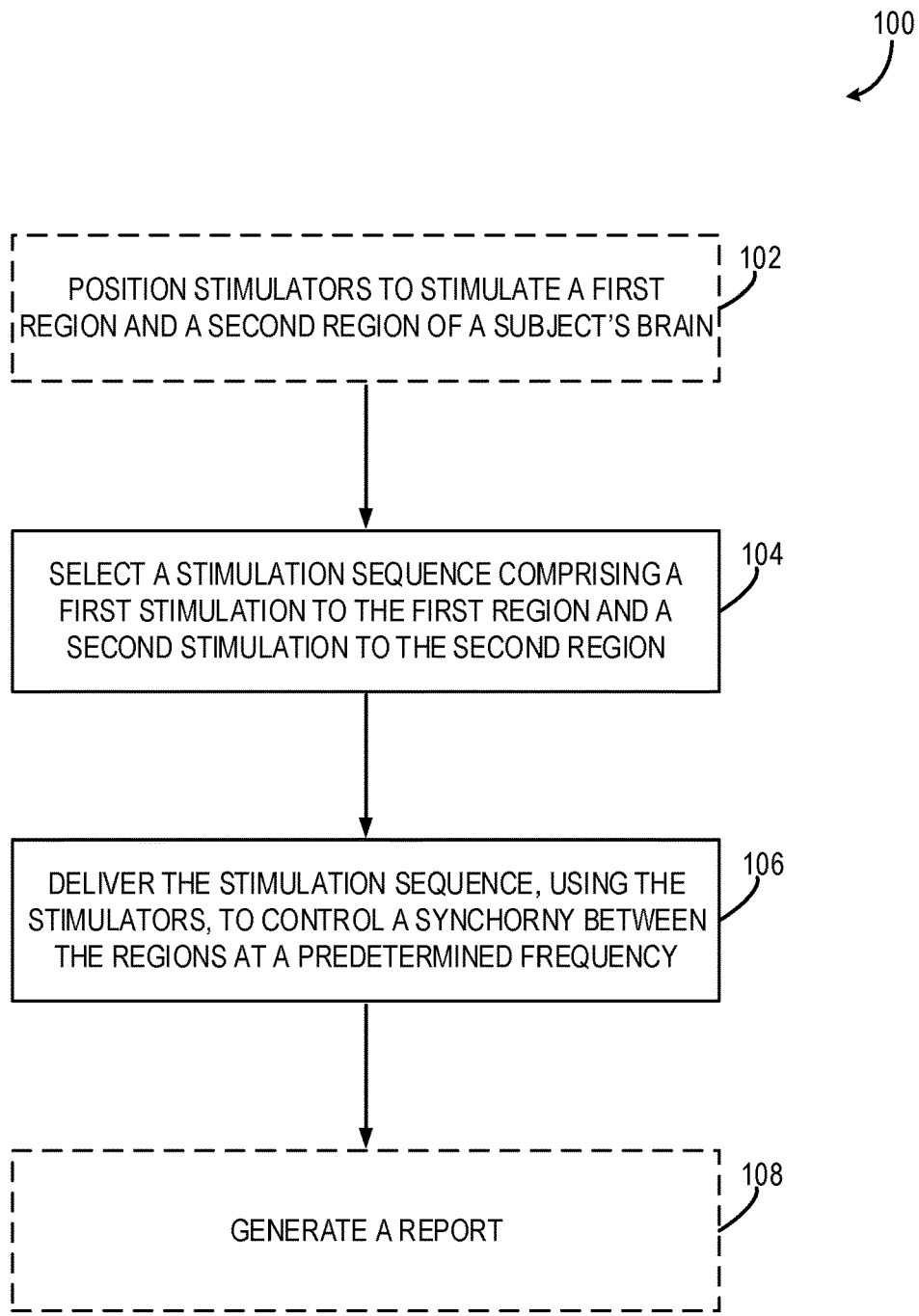
FIG. 1 is a flowchart setting forth steps of a process, in accordance with aspects of the present disclosure.

Turning now to FIG. 1, a flowchart setting forth steps of a process 100, in accordance with aspects of the present disclosure, is shown. The process 100, or steps therein, may be carried out using any suitable device, apparatus or system, such as systems in accordance with the present disclosure. In some aspects, the process 100 may be implemented as a program, software, or instructions stored in a memory, such as a non-transitory computer readable medium or other storage location, that are executable, at least in part, by a processor or computer.

The process 100 may optionally begin at process block 102 with positioning stimulators to stimulate a subject's brain. For example, electrodes or optical fibers may be implanted in subject's brain. In some aspects, as indicated by process block 102, a number of stimulators may be positioned to stimulate a first region and a second region of the subject's brain. Stimulators may also be positioned to stimulate fewer or more than two regions. However, positioning, or implantation, need not be carried out during execution process 100, but rather during a prior procedure or intervention.

At process block 104, a stimulation sequence, such as a pulsed stimulation sequence, may then be selected. By way of example, the stimulation sequence may include one or more stimulations, including electrical stimulations, that have a duration in a range between approximately 0.01 seconds and 10 seconds, a stimulation frequency in a range between approximately 0.1 Hz and 100 Hz, an intensity in a range approximately between 0.1 and 20 Volts, or alternatively approximately 1 to 100 mAmps, a pulse width in a range between approximately 0.1 and 250 microseconds, although other values may be possible, and various combinations thereof. In the present disclosure, the term approximately, when referring to a numerical value or range, may generally include positive and negative variations by up to 10% from the stated nominal values or range (high and low) values. Electrical, and other, stimulations may be monophasic or biphasic, with pulses having any waveform shape. Also stimulations may be pulsed, continuous, or intermittent in the form of currents or voltages, light, and so on, having various amplitudes, frequencies, periods, waveforms, durations, phases, polarities, and so on.

In accordance with aspects of the disclosure, a selected pulsed stimulation sequence includes a first stimulation to be delivered to the first region, and a second stimulation to be delivered to the second region of a subject's brain. As described, the first and second stimulation may be separated in phase by a variable phase difference, or phase lag. The first and second stimulation may be timed to be substantially concurrent, although they need not have the same stimulation parameters, such as duration, intensity, and so on. Fewer or more stimulations may also be possible, with each stimulation being defined by any combination of stimulation parameters, as described.

In some implementations, a user may select pre-programmed stimulation parameters, such as various target frequencies, intensities, durations, timings, and so on. Stimulation may also take into consideration a variety of information, including a condition or disorder of the subject, targeted structures or regions in the brain, and properties (e.g. electrical, optical, magnetic) of such regions. As such, a user may also provide selections indicative of such targeted regions, tissue properties, subject disorder or conditions, and so on. User selections may be provided via an input or user interface.

Other information useful for selecting a stimulation sequence may be based on data obtained from the subject. In particular, brain activity measurements, or brain signals, may be acquired and analyzed to determine various metrics of synchrony. Example measurements include local field potential (LFP) measurements, electroencephalogram (EEG) measurements, single-neuron measurements, multi-neuron measurements, spike measurements, optical measurements, sonic measurements and others. Metrics of synchrony computed may include coherences, cross-correlations, multi-signal computations, principal-component computations, and so on. In one aspect, coherences between targeted regions or brain circuit elements may be computed using respective LFP signals, which may then be used to determine a synchrony or a connectivity between them.

Using a determined synchrony and a target clinical endpoint, a phase lag between the first and second stimulation, for instance, along with targeted frequency or frequencies, may be determined. By way of example, the phase lag may be in a range between approximately 10 and 350 degrees, depending on the desired effect. In some aspects, the phase lag may be selected to determine a specific directionality for enhancing circuit connectivity. Other measurements, including, imaging, and others may also be taken into consideration when selecting the stimulation sequence.

Based on inputted selections, measurements, as well as information obtained therefrom, a stimulation sequence may be selected at process block 104. In some aspects, a reference or database, storing a variety of information including combinations of stimulation parameters corresponding to various conditions, measurements and information, may also be utilized in making the selection. As such, a user may be provided with such reference, database, or information therein. Alternatively, or additionally, a processor or controller may access such reference or database and make a selection or determination using information therein.

Referring again to FIG. 1, the selected stimulation sequence may then be delivered using the stimulators. To this end, the selected stimulation sequence may be utilized to control a stimulation system. The stimulation may be delivered once, or a number of times, over a selected or determined period of time. As an addition, or alternative to process block 106, a report may be optionally generated, as indicated by process block 108. The report may be in any form and include any information, including any stimulations, parameters thereof, or measurements acquired from a subject. In some aspects, the report may include the selected stimulation sequence in the form of instructions, executable by a stimulation system.

Figure 2:
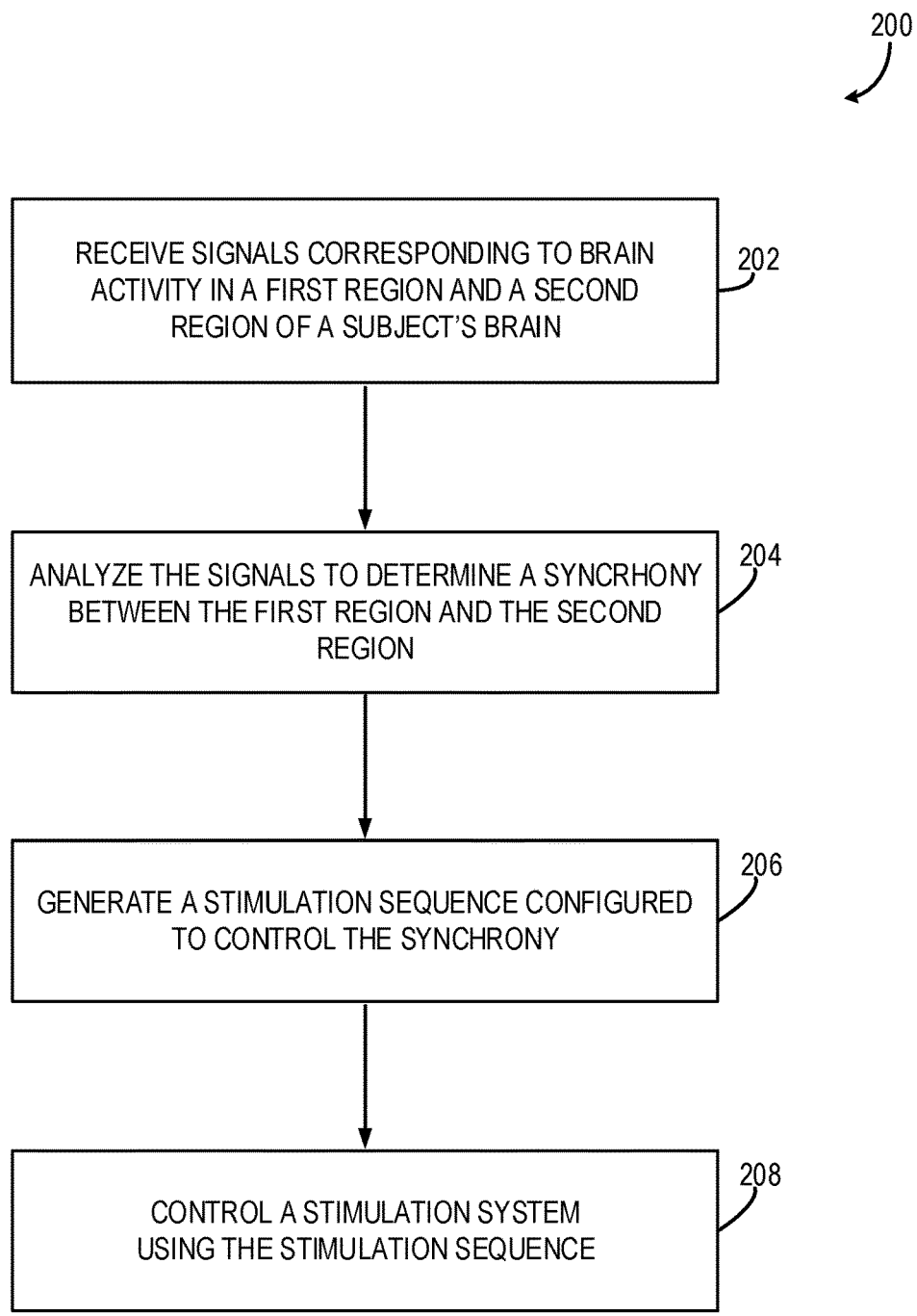
FIG. 2 is another flowchart setting forth steps of a process, in accordance with aspects of the present disclosure.

Turning now to FIG. 2, another flowchart setting forth steps of a process 200, in accordance with aspects of the present disclosure, is shown. Similarly, the process 200, or steps therein, may be carried out using any suitable device, apparatus or system, such as systems in accordance with the present disclosure. In some aspects, the process 200 may be implemented as a program, software, or executable instructions stored in a memory, such as a non-transitory computer readable medium, or other storage location. The process 200 may be carried out to control a stimulation system, in accordance with aspects of the present disclosure.

As shown, the process 200 may begin at process block 202 with receiving signals corresponding to brain activity of a subject. As described, this may include receiving various brain signals, such as LFP signals, acquired using electrodes positioned about a subject's brain. In some aspects, brain signals corresponding to a first region and a second region of the subjects' brain may be received. Then, at process block 202, the received signals may be analyzed to determine a synchrony therebetween. As indicated in FIG. 2, the synchrony between the first and second region may be determined at process block 204. This may include computing various metrics, such as coherences, cross-correlations, and other related multi-signal computations, using the signals. For example, an average spike rate, or a principal-component extracted from multiple signal channels may be computed. Other processing steps may also be carried out in the analysis step, including various filtering, amplification, transformation, and other processing steps.

A stimulation sequence may then be generated to control the determined synchrony, as indicated by process block 206. As described, the stimulation sequence may be described by various parameters, including various durations, frequencies, intensities, waveforms, and so on, and could be based on information provided by a user, as well as information determined from measurements obtained from the subject. In particular, in some aspects, the synchrony, or lack thereof, may be used to generate the stimulation sequence. For example, coherence values at various frequencies computed in the analysis carried out at process block 204 may be compared to a reference or values stored in a database. The reference values may be indicative of natural rhythms, synchrony or connectivity. A determination may then be made with regard to the frequencies, intensities, durations, and phase lags, required for an applied stimulation. Based on the comparison, and desired therapeutic effect, specific parameters may then be selected. Although analysis and processing are carried at steps 204 and 206, a display of the results, in the form of spectrogram or coherogram, or other visualization of the data, need not be provided.

The generated stimulation sequence may then be used to control a stimulation system, as indicated by process block 208. To this end, the generated stimulation sequence may be provided in a report, in the form of instructions, executable by the stimulation system. Other information may also be provided in the report, as described.

Figure 3:
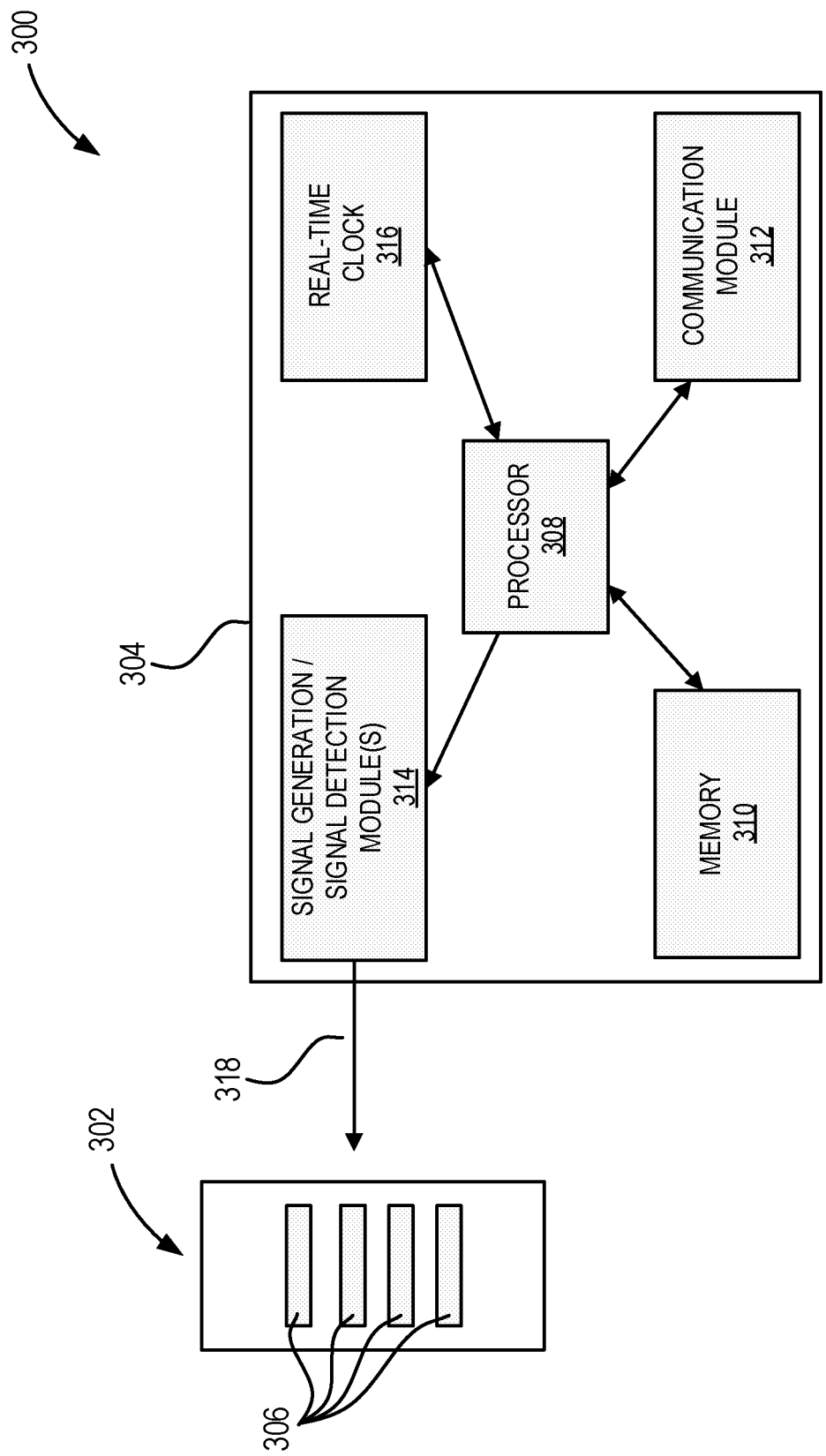
FIG. 3 is an illustration of a stimulation system, in accordance with aspects of the present disclosure.

Referring now to FIG. 3, an example stimulation system 300, in accordance with aspects of the present disclosure, is shown. As shown, the system 300 may generally include a stimulation assembly 302, and a controller 304 in communication with the stimulation assembly 302. Specifically, the stimulation assembly 302 may include a number of stimulators 306 configured to deliver stimulations to control brain activity in the subject. The stimulators 306 may include various electrodes, or probes with electrical contacts, configured for delivering electrical stimulations to the subject. Examples, include micro electrodes, deep brain stimulation electrodes, electrocorticography (ECoG) arrays, electroencephalogram (EEG) electrodes, and the like. In some implementations, the stimulators 306 may be configured to provide other types of stimulations, including magnetic stimulations, for example using magnetic stimulation coils, and optical stimulations, for example, using optogenetic fibers, actuators, and the like. In addition, the stimulation assembly 302 may also include various detectors or sensors capable of measuring brain activity in the subject. Non-limiting examples, include electrical leads or contacts, magnetic detectors, optical detectors, and so forth. The stimulation assembly 302, or stimulators 306 therein, may be wholly or partially implanted in a patient's skull, scalp, or both. Depending on the mode of stimulation, the stimulation assembly 302 may also utilize various methods and structures to support and couple the stimulators 306 and detectors to the subject.

As shown in FIG. 3, the controller 304 may generally include a processor 308, a memory 310, such as flash or other type of memory, a communication module 312, signal generation/signal detection modules 314, a real-time clock 316, and optionally a power source (not shown). As shown, the controller 304 may also include various connections, or terminals 318 for transmitting signals generated by the signal generation module 314. Any or all of these elements may be implanted into a patient's body or carried/worn externally to the body, or some elements may be used in each configuration with an appropriate interconnection system.

In some implementations, the controller 304 may also include an input for accepting user selections, operational instructions and information, as well as an output or display for providing a report. Specifically, the input may include various user interface elements, such as a mouse, keyboard, touchpad, touch screen, buttons, and the like. The input may also include various drives and receptacles, such as flash-drives, USB drives, CD/DVD drives, and other computer-readable medium receptacles, for receiving various data and information. To this end, the input may also include various communication ports and modules, such as Ethernet, Bluetooth, or WiFi, for exchanging data and information with various external computers, systems, devices, machines, mainframes, servers or networks.

The processor 308 can be configured or programmed to perform a variety functions for operating the controller 304 using instructions stored in memory 312, in the SUBSTITUTE SHEET (RULE 26) form of a non-transitory computer readable medium, or instructions received via input. In some implementations, the processor 308 may control the sending and receiving of instructions and operational parameters (for example, via a wireless transcutaneous link in the communication module 312), the storage of the operational or stimulation parameters and instructions in memory 310, the transmission of the operational parameters to signal generators in the signal generation module 314, the selective triggering of the signal generators to provide electrical, and other stimulations, to various brain regions or tissues of a subject, as well as synchronizing various functions using the real-time clock 316. For instance, the processor 308 may communicate with the real-time clock 316 to determine the timing, phase lag, and synchronization of various stimulations. The processor 308 may also communicate with the real-time clock 316, as well as other hardware and digital logic circuitry, to accurately store activation times in memory 310 and provide activation counts. By way of example, the processor 308 can be a programmable microprocessor or microcomputer.

The signal generation module 314, in communication with the processor 308, may include a number of signal generators for providing activating signals to the stimulators 306. In some implementations, each of the stimulators 306 may be individually controlled using separate signal generators. The signal generators can be independently operated, either sequentially or concomitantly, by the processor 308, to provide stimulation signals with various intensities, frequencies, phases, pulse widths, durations and waveforms. In some aspects, the signal generators may be controlled to provide stimulations to various brain regions substantially concurrently, using selected phase lags. For instance, a first stimulation may be provided to a first region in the subject's brain, while a second stimulation may be provided to a second region. In addition, in some implementations, the signal generation module 314 may include an output sensing circuit to monitor contact output, as well as other fail-safe mechanisms. This may be desirable, for instance, in order to mediate timed switching for biphasic pulsing.

The signal detection module 314 may include various hardware, and be configured to detect brain signals acquired using the stimulation assembly 302. For instance, the signal detection module 314 can include various analog-to-digital converters, voltage/current meters, amplifiers, filters, and other elements. Signals from the signal detection module 314 may then be provided as input and processed by the processor 308. Alternatively, the signals may be stored in the memory 310 and subsequently accessed/processed by the processor 308.

In some aspects, the processor 308 may receive signals corresponding to brain activity in a first region and a second region of a subject's brain as input. The processor 308 may then analyze the signals to determine a synchrony between the regions, for example, by computing various metrics indicative of synchrony, such as coherence and others, as described. Based on the analysis, as well as other provided or determined information, the processor 308 may then determine or select a stimulation sequence configured to control the synchrony. In some aspects, the processor 308 may receive such information from various input elements configured on the controller 304, as described, or alternatively from an external or remote device, computer or system, by way of the communication module 312. The processor 308 may also access a reference or database, as described, stored locally in the memory 310, or at storage location. In some implementations, the processor 308 may operate in an open-loop or a closed-loop fashion to control brain activity in a subject.

In some aspects, the stimulation sequence determined or selected by the processor 308 may be a pulsed stimulation sequence that includes first stimulation to the first region and a second stimulation to the second region, with the stimulations being timed to be substantially concurrent and separated by a phase lag. Herein, substantially concurrent generally refers to the stimulations being initiated at approximately the same starting time. In some aspects, the stimulations may be initiated within 5 seconds or less of each other, although other values may be possible. The processor 308 may then direct the signal generation module 314 to deliver the pulsed stimulation sequence.

In some implementations, the controller 304, along with the stimulation assembly 302, may be part of a standalone stimulation system. Alternatively, the controller 304 may be a wearable or implantable unit that is programmable or configurable using an external device, computer or system. To this end, the communication module 312 may be configured to send and receive various signals, as well as receive power. Specifically, the communication module 312 may include an antenna, or an input-output wire coil, a receiver and transmitter, data converters, as well as other hardware components. As a non-limiting example, the receiver and transmitter may be configured to receive and transmit radio-frequency (RF) signals. In some implementations, the antenna may be configured for transcutaneous wireless two-way communication with an external wearable device, sending and receiving signals when the external wearable device is placed in close proximity. The communication signals may be transmitted through magnetic induction and include information for operating and/or programming the processor 308. For instance, the communication signals may include triggers or command signals for generating stimulations. In some aspects, transmitted signals may also be configured to power or recharge battery components powering the controller 304. The antenna may be connected to a receiver and transmitter, which in turn may be connected to serial-to-parallel and parallel-to-serial data convertors, respectively. Any information sent or received, as described, may then be processed by the processor 308.

As mentioned, the controller 304 may be powered by an internal and/or external power source. For example, an internal source may include a standard rechargeable battery, comparable to batteries used in implantable devices (e.g., pacemakers). Alternatively, or additionally, the internal power source may include a capacitor in combination with a regulator, such as a single ended primary inductor converter or dc-dc converter, that together can generate a constant current or voltage output for short periods of time. In some implementations, the capacitor may be charged by an external wearable device. As such, the controller 304 may include an induction coil, or thin, tightly wound wire that allows for RF telemetry and/or battery recharge by an external wearable device, configured either as part of the communication module 312, or as separate hardware. Other methods of charging may also be utilized.

Figure 4:
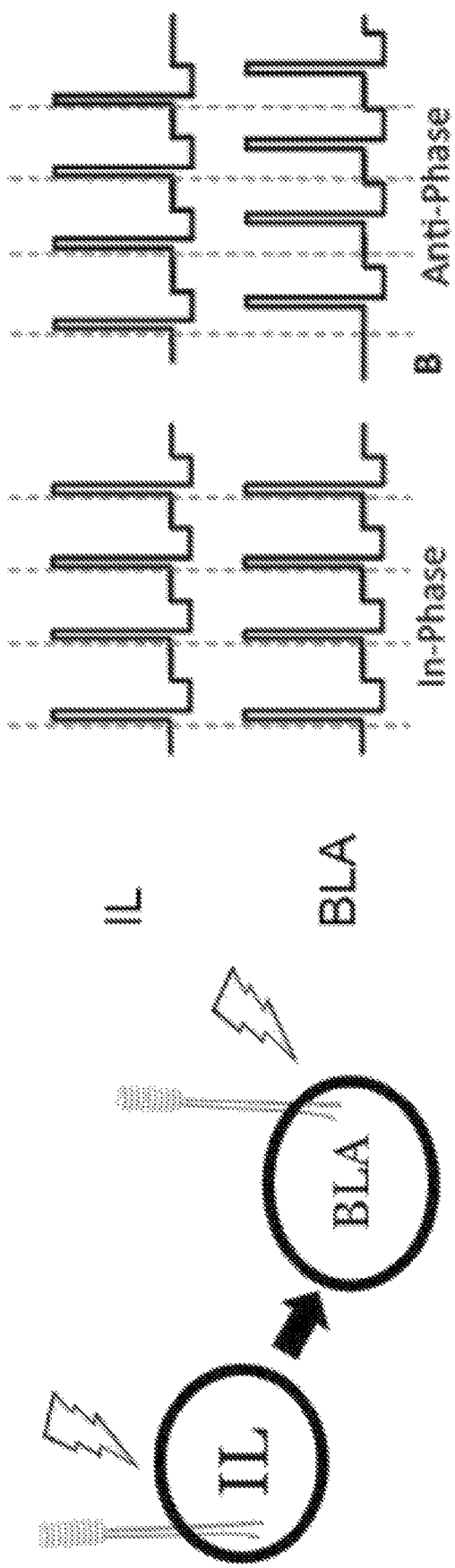
FIG. 4 is a schematic diagram of the stimulation system shown in FIG. 3.

By way of example, the present approach was utilized to alter oscillatory synchrony in brain activity of rodent models. Specifically, paired electrical stimulations were provided to fronto-limbic circuits, aiming to enhance low-frequency theta band (4-8 Hz) oscillations between a first region, namely the infralimbic cortex (IL), and second region, namely the basolateral amygdala (BLA), which are involved in clinically relevant fear-behavior regulation. As illustrated in FIG. 4, two-channel platinum/iridium electrodes were implanted into the IL and BLA of Long-Evans rats. Stimulation parameters were varied, yielding a total of 72 parameter sets. Electrical stimulations included single-site stimulations at the IL and BLA, along with double-site, paired stimulations both to the IL and BLA, using in-phase and anti-phase stimulation sequences applied substantially concurrently, as shown in FIG. 4. As shown, anti-phase, or phase lagged, stimulations were provided to the BLA at later time points. Voltages used included 0.5 V, 1 V and 2 V, and stimulation durations included 0.5 seconds, 1 second and 1.5 seconds. In addition, phase angle lag between the paired stimulations included 0, 90, 180 and 270 degrees. The stimulation frequency was performed at 6 Hz.

For each experimental session, the order of parameter-set testing was randomized. Five repeated consecutive stimulations were delivered within each parameter set and the LFP signals were recorded from both IL and BLA throughout the entire experiment. Each recording session yielded a continuous time-series of data. The stimulation events were separated into trials, aligned to the onset of stimulation, and analyzed based on the different parameter sets. Time-frequency and coherence analysis was performed to study the entrainment effects at different dosages. The directionality of coherence was quantified using a correlation lag technique.

Figure 5:
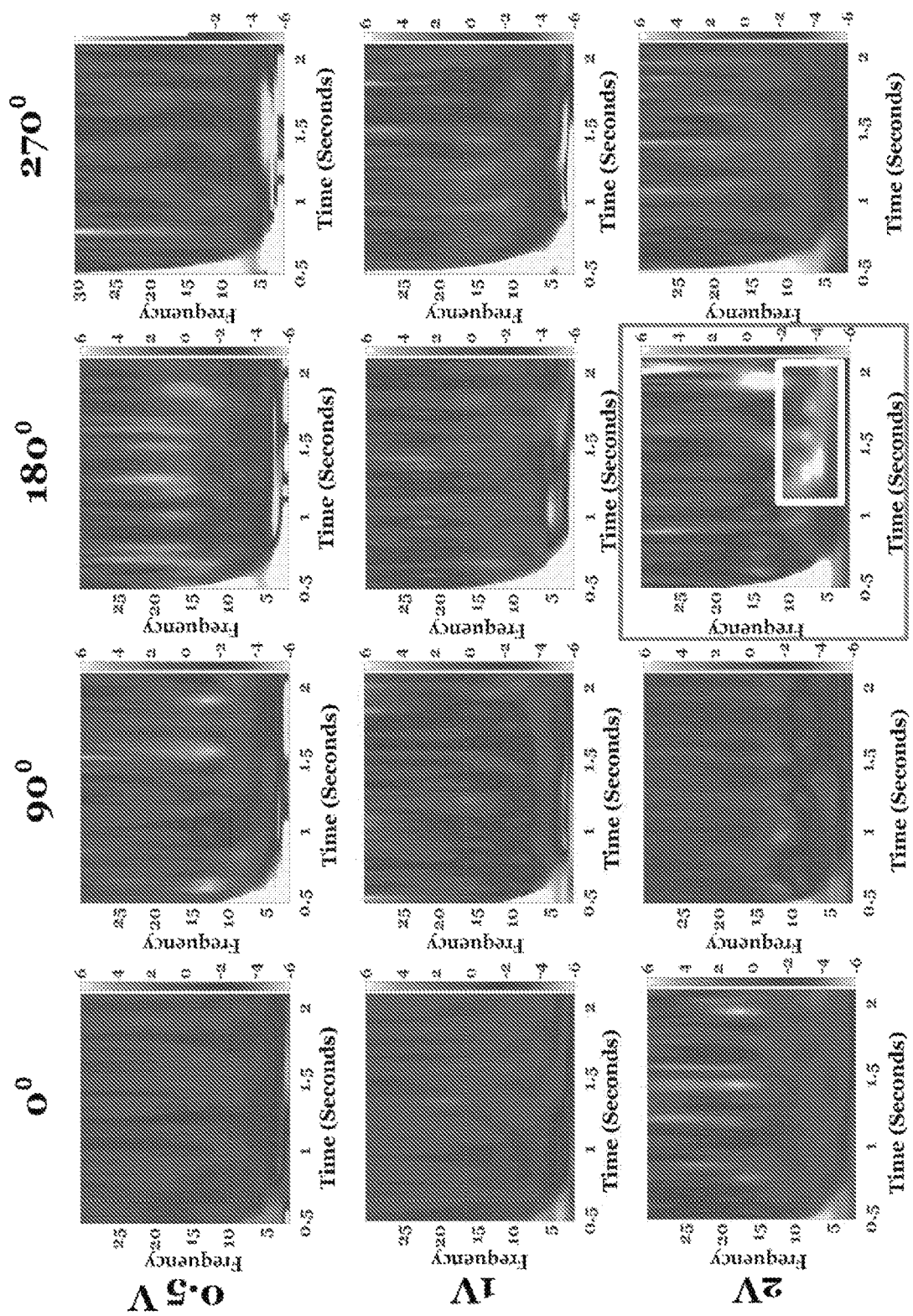
FIG. 5 are example graphs showing increases in coherence achieved in an animal model using paired electrical stimulations, in accordance with aspects of the present disclosure.
Figure 6A:
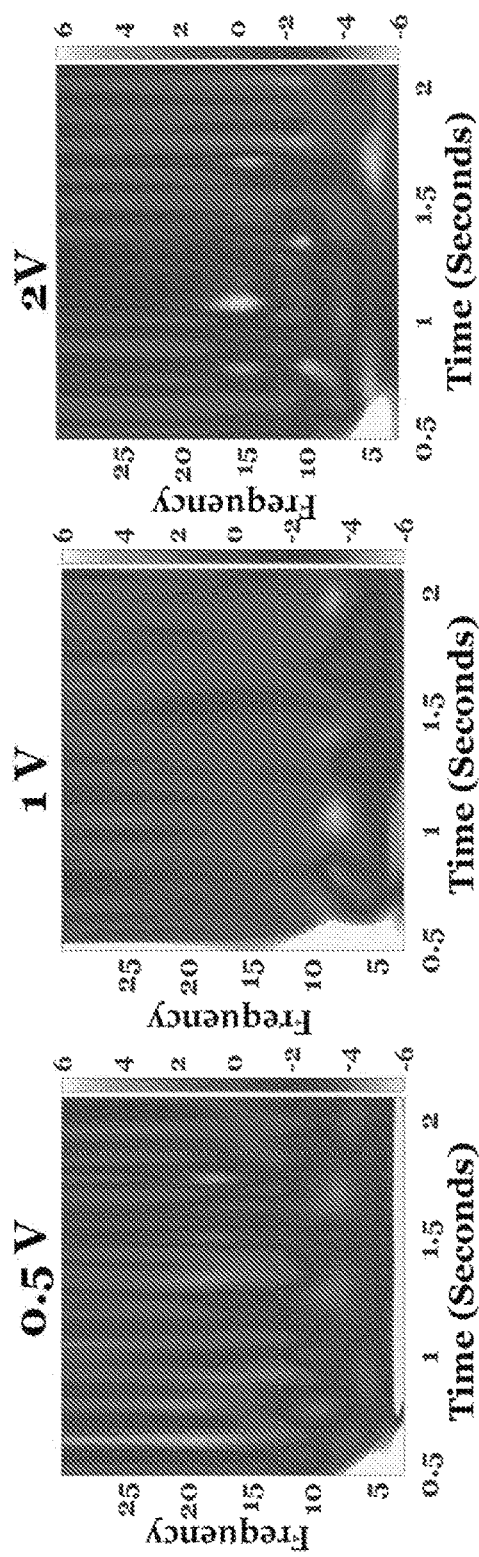
FIG. 6A shows example graphs indicating that single site stimulation do not induce coherence changes.
Figure 6B:
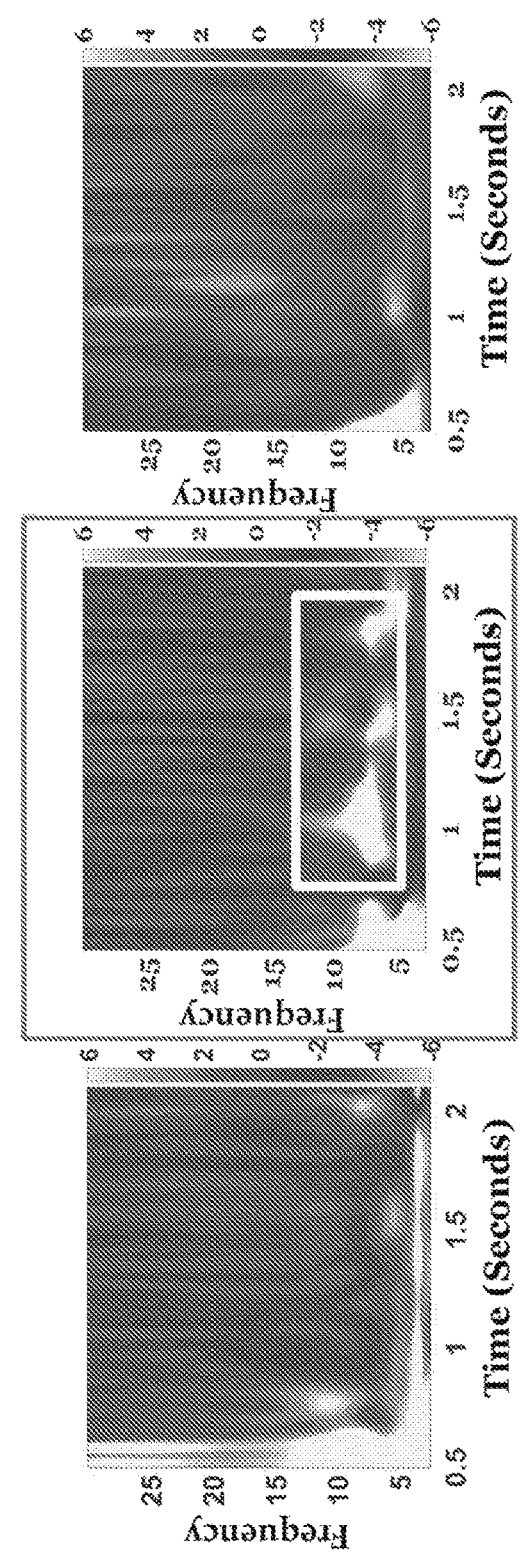
FIG. 6B shows other example graphs indicating that single site stimulation do not induce coherence changes.

Results are shown in FIGS. 5, 6A and 6B. Specifically FIG. 5 shows coherence graphs obtained using varied intensities and phase lags, with stimulation duration selected to be 0.5 seconds. As appreciated from FIG. 5, paired IL-BLA stimulation with a lag of 180 degrees, with IL leading, increases IL-BLA coherence. The color axis in the figure represents z-score over the pre-stimulation baseline for over 30 trials per figure. The coherence changes were observed in the shorter (0.5 seconds), rather than the longer (1 and 2 seconds) stimulation duration. By contrast, single site stimulation at the IL and BLA, FIGS. 6A and 6B, respectively, do not induce coherence changes.

Figure 7A:
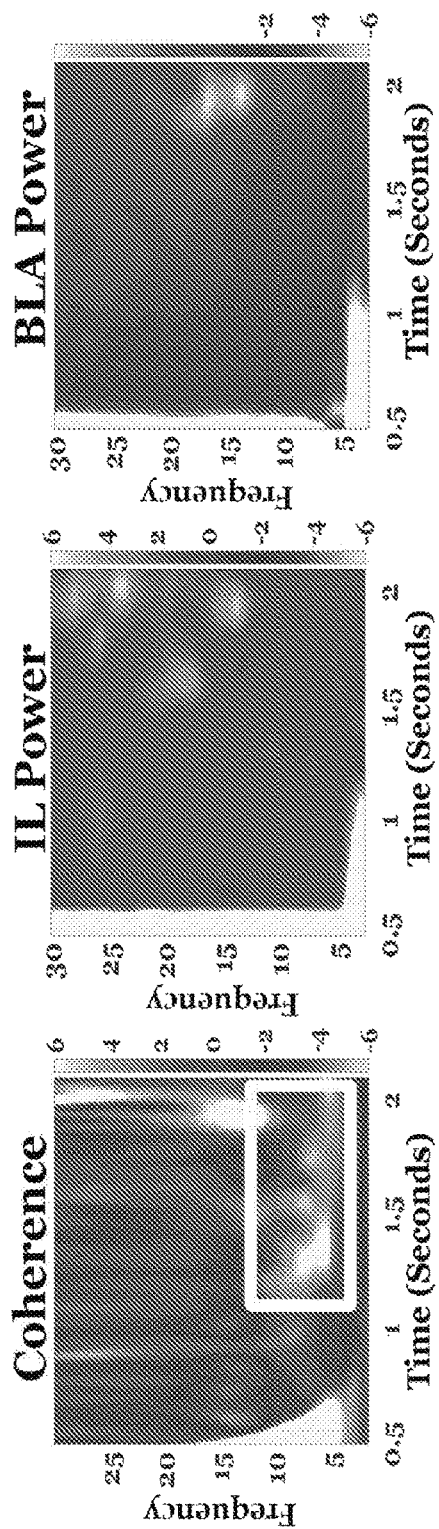
FIG. 7A shows example graphs indicating that coherence change is not drive by amplitude changes.
Figure 7B:
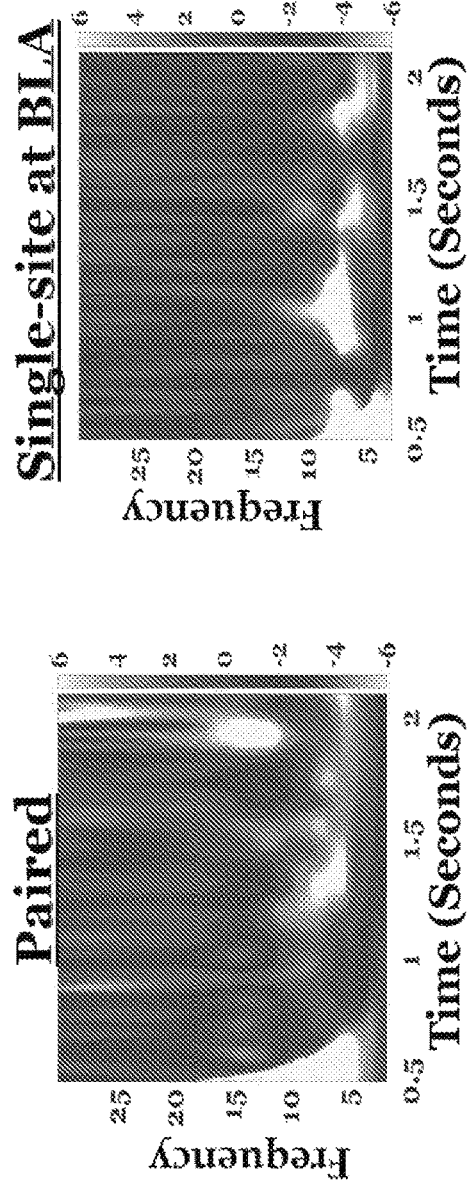
FIG. 7B shows example graphs indicating that paired stimulation induces top-down coherence, in accordance with aspects of the present disclosure, while single-site stimulation induces bottom-up coherence.

In addition, coherence changes are not driven by amplitude changes of the local IL or BLA LFP signals, as appreciated from FIG. 7A, showing results for 0.5 second paired stimulation, using 2V and 180 degree lag. Furthermore, paired stimulation, according to methods described herein, induce top-down IL to BLA coherence, whereas single-site stimulation to the BLA produces bottom-up BLA to IL coherence, as appreciated from FIG. 7B.

Figure 8:
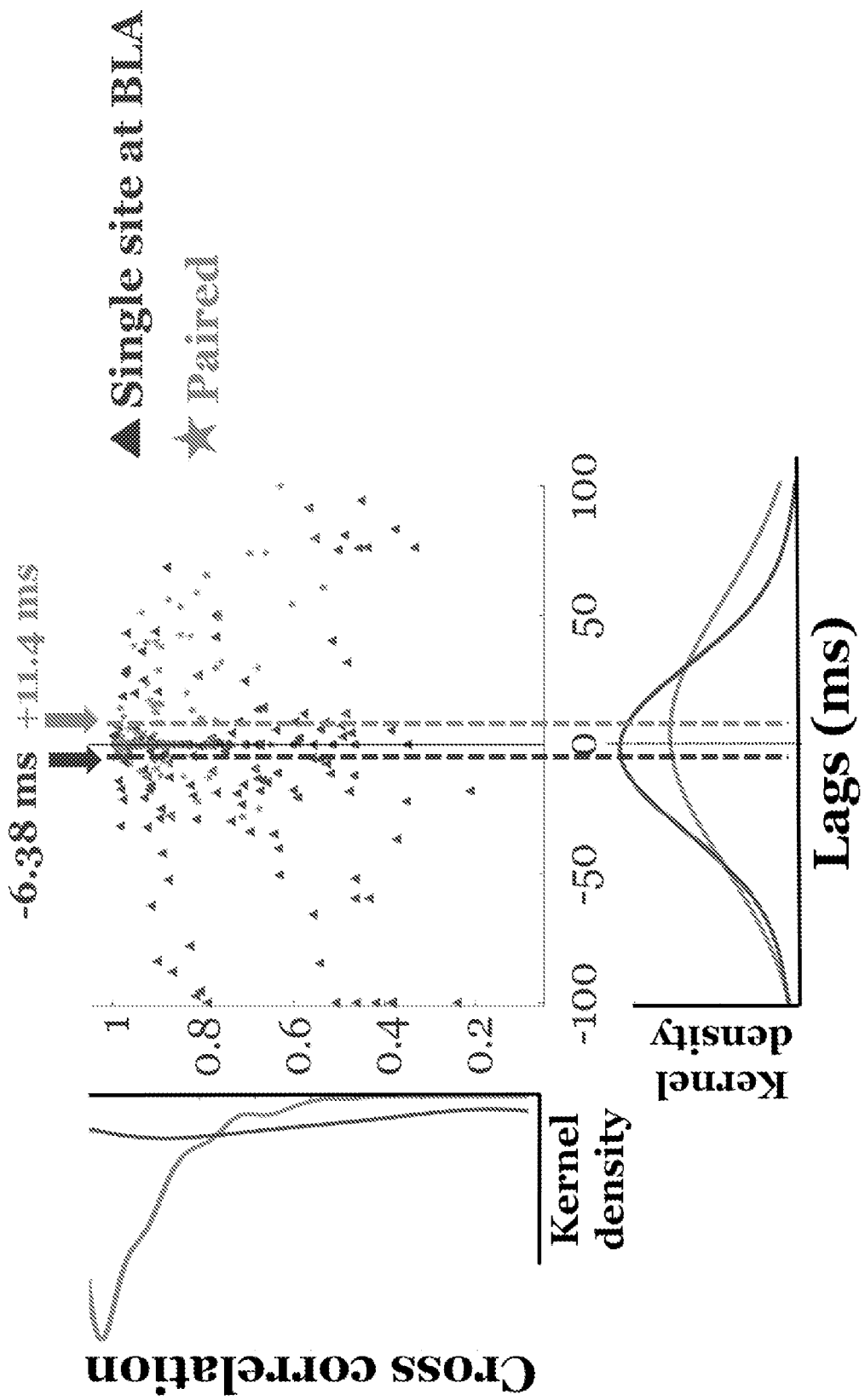
FIG. 8 is a graphical illustration showing that paired stimulation induces directional (top-down) coherence that is not possible with single-site stimulation.

Further, the coherence change induced by phase-lagged stimulation has directionality, such that communication may be enhanced from the first to the second brain region but not from the second to the first. FIG. 8 shows the cross-correlation between theta-band filtered LFP of IL and BLA after administering the phase-lagged stimulation as diagrammed in FIG. 4. The scatter plot shows the peak lag of cross-correlation for individual stimulation trials, while the plots on the X and Y axis summarize the group-level distribution of those trials. The peak cross-correlation value was much higher (close to 1) for paired than for a single-site stimulation, verifying that this is a method for increasing inter-region synchrony. Further, the lag distribution for paired stimulation had a peak at a positive lag, ~11.4 ms. This illustrates top-down connectivity from IL to BLA, a circuit change that should be beneficial in treatment of emotional disorders.

Results shown here illustrate that paired stimulation with 180 degree lag between IL and BLA stimulation trains can induce coherence changes, with directionality, lasting beyond the end of the stimulation. This indicates that paired stimulations may be used to alter brain oscillatory synchronies.

Figure 9:
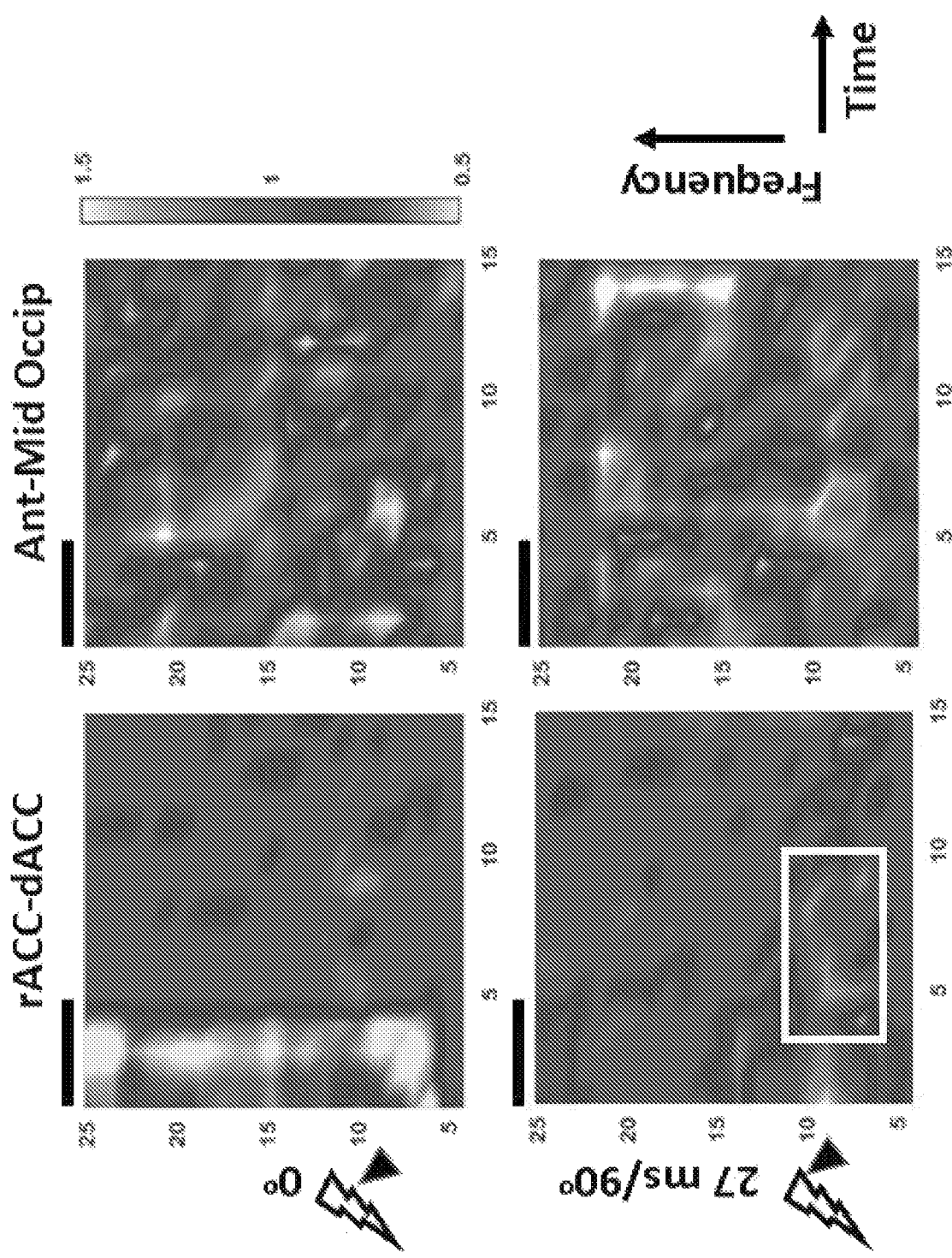
FIG. 9 are example graphs showing increases in coherence achieved in human volunteer using paired electrical stimulations, in accordance with aspects of the present disclosure.

The present approach was further validated in a human volunteer. Specifically, a stimulation was applied to widely separated sites in the rostral and dorsal anterior cingulate cortex, namely the rACC and dACC. When stimulation was tuned to an alpha frequency (i.e ~9 Hz) and the lag between the rACC and dACC pulses was 90 degrees (i.e. ~28 ms), there was a specific, band-limited increase in alpha coherence that lasted beyond the stimulation period, as shown in FIG. 9. These results indicate that the connectivity between different brain networks may be enhanced, and directionally controlled, using the present approach. They further demonstrate that the method of the present disclosure is not limited to a particular frequency band or phase lag.

Figure 10:
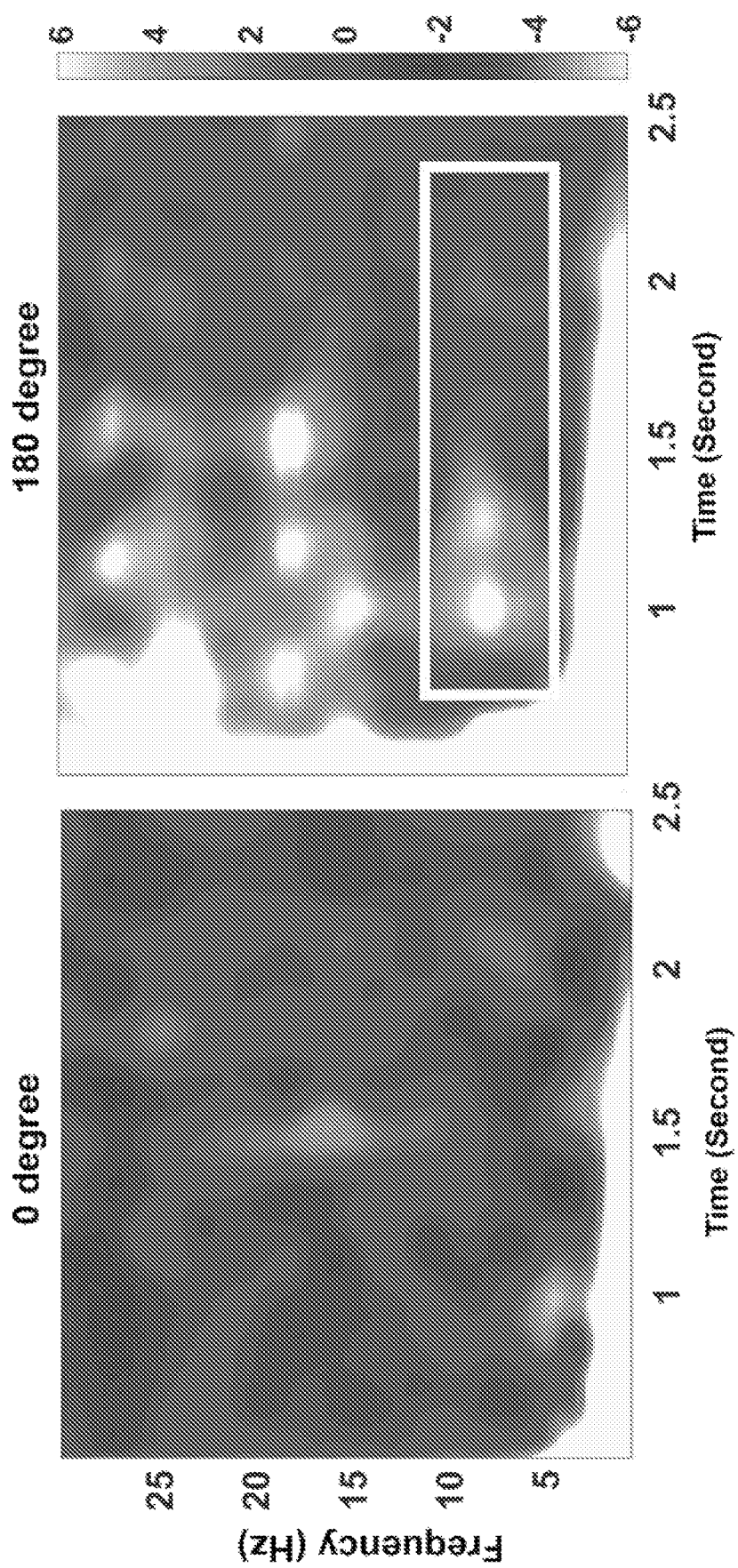
FIG. 10 are example graphs comparing effects on coherence achieved in an animal model using paired electrical stimulations with different phase lags, in accordance with aspects of the present disclosure.
Figure 11:
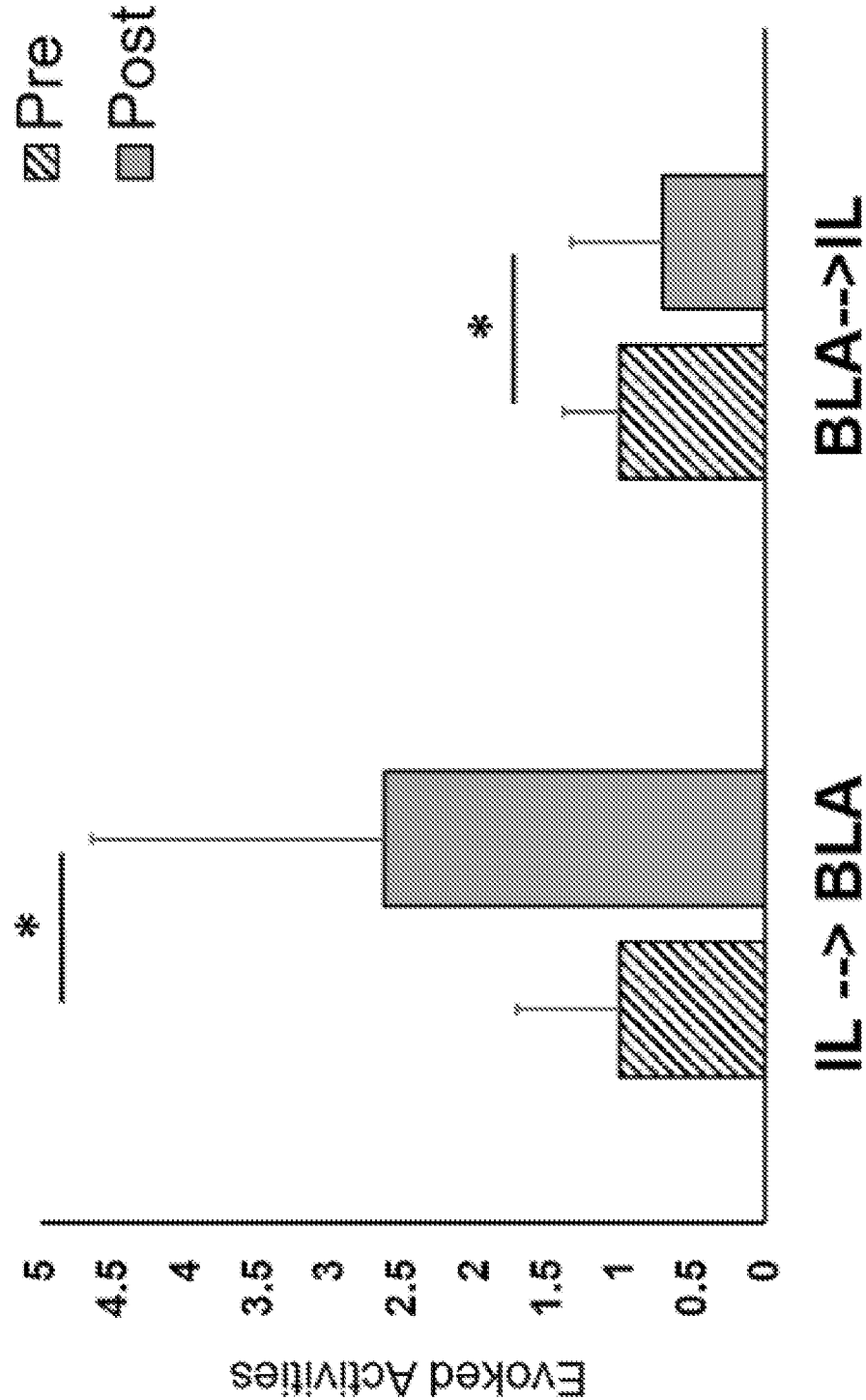
FIG. 11 is a graph showing evoked activities before and after paired stimulations, in accordance with aspects of the present disclosure.

In another example, an electrical stimulation sequence of 500 ms and 6 Hz biphasic electrical pulse trains was simultaneously into both the infralimbic cortex (IL) and the basolateral amygdala (BLA) in 3 animals and across multiple days. When the BLA train was 180° (83 ms) lagged to the IL train, a large coherence increase was observed and lasted ~1 second post stimulation (FIG. 10). The effects were specific to the stimulation frequency and its harmonics, did not affect nearby frequencies and could be repeatedly induced over multiple days. The stimulation protocol also changed IL-BLA connectivity. The BLA response to an IL stimulus became stronger and the IL response to a BLA stimulus became weaker post electrical stimulation (FIG. 11). The top-down strengthening connectivity could be beneficial as it is associated with healthy emotion regulation in human.

As appreciated from description above, herein provided systems and methods utilize a novel approach and have a broad range of applications, including for treatment of patients with various neurological and psychiatric disorders. Features suitable for such combinations and sub-combinations would be readily apparent to persons skilled in the art upon review of the present application as a whole. The subject matter described herein and in the recited claims intends to cover and embrace all suitable changes in technology.

The invention claimed is:

1. A method for controlling a synchrony in brain activity of a subject, the method comprising:
   positioning stimulators to stimulate a first region and a second region of a subject's brain;
   receiving signals corresponding to brain activity in the first region and the second region;
   analyzing the signals to determine a synchrony between the first region and the second region;
   selecting a pulsed stimulation sequence comprising a first stimulation to the first region and a second stimulation to the second region, wherein the stimulations are timed to be substantially concurrent and separated by a phase lag,
      the phase lag being selected based on the determined synchrony; and
   delivering the pulsed stimulation sequence, using the stimulators, to control the synchrony between the first region and the second region at a predetermined frequency.

2. The method of claim 1, wherein the method further comprises detecting brain signals associated with first region and the second region.

3. The method of claim 2, wherein the method further comprises computing a metric of the synchrony using the brain signals detected.

4. The method of claim 3, wherein the method further comprises generating a report indicative of the synchrony measured.

5. The method of claim 1, wherein the method further comprises selecting the pulsed stimulation sequence to have a duration in a range between 0.1 seconds and 10 seconds.

6. The method of claim 1, wherein the predetermined frequency is in a range between 0.1 Hz and 100 Hz.

7. The method of claim 1, wherein the method further comprises selecting the phase lag between the first stimulation and the second stimulation to be in a range between 10 and 350 degrees.

8. The method of claim 1, wherein the method further comprises selecting the pulsed stimulation sequence to have an intensity in a range between 0.1 and 20 Volts.

9. A method for controlling a stimulation system, the method comprising:
   receiving signals corresponding to brain activity in a first region and a second region of a subject's brain;
   analyzing the signals to determine a synchrony between the first region and the second region;
   generating a pulsed stimulation sequence configured to control the synchrony, wherein the stimulation sequence comprises a first stimulation to the first region and a second stimulation to the second region, with the stimulations being timed to be substantially concurrent and separated by a phase lag,
      the phase lag being selected based on the determined synchrony; and
   controlling a stimulation system using the pulsed stimulation sequence.

10. The method of claim 9, wherein the method further comprises detecting the brain activity by measuring local field potential (LFP) signals associated with the first region and the second region using the electrodes.

11. The method of claim 10, wherein the method further comprises computing a coherence between the LFP signals detected to determine the synchrony.

12. The method of claim 9, wherein the method further comprises selecting the pulsed stimulation sequence to have at least one of duration in a range between 0.1 seconds and 10 seconds, a stimulation frequency in a range between 0.1 Hz and 100 Hz, and an intensity in a range between 0.1 and 20 Volts.

13. The method of claim 9, wherein the method further comprises selecting the phase lag to be in a range between 10 and 350 degrees.

14. A system for controlling a stimulation provided to a subject, the system comprising:
   an input configured to receive signals acquired from a subject's brain;
   a processor configured to:
      receive signals from the input corresponding to brain activity in a first region and a second region of a subject's brain;
      analyze the signals to determine a synchrony between the first region and the second region;
      determine a pulsed stimulation sequence configured to control the synchrony, wherein the stimulation sequence comprises a first stimulation to the first region and a second stimulation to the second region, with the stimulations being timed to be substantially concurrent and separated by a phase lag,
         the phase lag being selected based on the determined synchrony; and
      direct a signal generation module in communication with the processor to deliver the pulsed stimulation sequence.

15. The system of claim 14, wherein the processor is further configured to control an acquisition of local field potential (LFP) signals associated with the first region and the second region using the electrodes.

16. The system of claim 14, wherein the processor is further configured to compute a coherence between local field potential (LFP) signals detected to determine the synchrony.

17. The system of claim 14, wherein the processor is further configured to select the pulsed stimulation sequence to have at least one of duration in a range between 0.1 seconds and 10 seconds, a stimulation frequency in a range between 0.1 Hz and 100 Hz, and an intensity in a range between 0.1 and 20 Volts.

18. The system of claim 14, wherein the processor is further configured to select the phase lag to be in a range between 10 and 350 degrees.

* * * * *